US00PP11290P

United States Patent [19]

Stravers

[11] Patent Number: Plant 11,290

[45] Date of Patent: Mar. 14, 2000

[54] GERBERA PLANT NAMED 'TERWISH'

[75] Inventor: Lambertus Johannes Maria Stravers, NG Kudelstaart, Netherlands

[73] Assignee: Terra Nigra Holding B.V., De Kwakel, Netherlands

[21] Appl. No.: 09/048,203

[22] Filed: Mar. 26, 1998

[51] Int. Cl.[7] ..... A01H 5/00

[52] U.S. Cl. ..... Plt./357

[58] Field of Search ..... Plt./357

[56] References Cited

U.S. PATENT DOCUMENTS

P.P. 7,245 6/1990 Segers ..... Plt./357

P.P. 7,281 7/1990 Segers ..... Plt./357

OTHER PUBLICATIONS

Huxley, Anthony, ed., The New RHS Dictionary of Gardening, vol. 2, Stockton Press, NY, p. 402, 1992.

*Primary Examiner*—Howard J. Locker
*Assistant Examiner*—Wendy A Baker

[57] ABSTRACT

A new and distinct cultivar of Gerbera plant named 'Terwish', as illustrated and described, characterized by its semi-double type, shining dark red ray florets which are a solid dark red color throughout, yellowish green disc before flowering of the individual disc florets with an overall flower diameter of 120 mm.

1 Drawing Sheet

BACKGROUND OF THE INVENTION

The present invention comprises a new and distinct cultivar of *Gerbera jamesonii*, referred to by the cultivar name 'Terwish'.

'Terwish' was originated from a hybridzation program in De Kwakel, The Netherlands in 1995. The female parent was unnamed seedling '94.156' (unpatented) and the male parent was 'Venus' (unpatented). The female parent '94.156' differs in flower type (single), color of the disc before flowering (dark i.s.o. yellowish green) and it has a longer stem. It has not been available outside Terra Nigra B.V. The male parent 'Venus' is semi-double and a bi-color (pink inner ray florets and creamy white outer ray florets). The new cultivar was selected by me from the progeny of the stated parentage on or about February 1996. The first asexual reproduction of 'Terwish' was accomplished when vegetative cuttings were taken on May 1996 in De Kwakel. The new cultivar is presently being propagated by cuttings and tissue culture. Horticultural examination of selected units initiated in 1997 has demonstrated that the combination of characteristics as herein disclosed for 'Terwish' are firmly fixed and are retained through successive generations of asexual reproduction.

'Terwish' has not been observed under all possible environmental conditions. The phenotype may vary significantly with variations in environment such as temperature, light intensity and day length. The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terwish', which in combination distinguish this Gerbera from its parents and all other varieties of which I am aware:

1. Type: Semi-double.
2. Color of ray floret: Dark red.
3. Color of disc before opening of disc florets: Green/yellow, R.H.S. 151A: innerpart (50%); outerpart: R.H.S. 199A.
4. Color of perianth lobe: Green, R.H.S. 137B.
5. Diameter of flower head: 120 mm.

Of the many commercial cultivars known to me, there is no cultivar similar in comparison to 'Terwish'.

BRIEF DESCRIPTION OF THE DRAWINGS

The accompanying photographic drawings show typical inflorescence and foliage characteristics of the new cultivar with the colors being shown as nearly true as is reasonably possible to attain in illustrations of this type.

The top photograph illustrates the flower head pictured across face.

The photograph at the bottom illustrates a typical leaf of the present invention.

BOTANICAL DESCRIPTION OF THE PLANT

Botanical: *Gerbera jamesonii* cv. 'Terwish'

In the following description, color references are made to The Royal Horticultural Society Colour Chart (R.H.S.). The color values were determined at 14:00 p.m. on Jan. 26, 1998 under artificial light at De Kwakel.

The following traits have been repeatedly observed and are determined to be basic characteristics of 'Terwish', which in combination distinguish this Gerbera as a new and distinct cultivar.

INFLORESCENCE

A. Flowerhead:

*Type.*—Semi-double.

*Diameter.*—Large (approx. 120 mm).

*Color (general tonality from a distance of* 3 *meters*).—Dark red.

*Shape.*—Incurving funnel-shaped.

*Involucre.*—Height from point of attachment of involucre to top of flower head: medium (approx. 37 mm). Height: medium (approx. 20 mm). Diameter: medium (approx. 40 mm). Number of bracts: high (approx. 95). Longitudinal axis of inner rows: mostly straight. Anthocyanin: absent. Pubescence: dense.

*Ray florets.*—Number: medium (55). Shape: obovate. Longitudinal axis outer row: incurving. Longitudinal axis inner row: incurving. Longitudinal axis of ray female floret: straight-reflexing.

*Outer ray floret.*—Cross section: flat. Length: medium (approx. 45–50 mm). Width: medium (approx. 14 mm). Longitudinal folding: medium. Angle of apex: acute. Shape of apex: pointed. Incisions of apex: 1–2. Depth of incision: shallow. Color (topside): R.H.S. 46A. Color (bottom side): R.H.S. 12C (30%), R.H.S. 48B mixed. Color distribution on inner side: uniform. Edge of different color: absent. Striation: absent. Claw spot: absent.

B. Disc florets:

*Disc diameter.*—Medium (approx. 30 mm).

*Color* (*immature, bottom*).—Yellowish green (50% at bottom, R.H.S. 154D).

*Color* (*immature, top*).—R.H.S. 187B.

*Main color upperside corolla.*—Female flowers: dark red (R.H.S. 46A). Male flowers: dark red (R.H.S. 46A).

C. Reproductive organs:

*Style.*—Main color distal part: soft pink (R.H.S. 39C).

*Stigma.*—Main color: white (R.H.S. 155A).

*Anthers.*—Main color: dark yellow (R.H.S. 15A). Color of top relative to other parts is darker, R.H.S 152A, 20%. Longitudinal stripes are absent. Intensity of anthocyanin coloration is absent.

*Pappus.*—Main color: greenish white R.H.S. 2D. Color of top relative to other parts is identical. Level of top relative to closed disc florets: above.

*Fertility.*—Fertility as well as the seedsetting is good.

D. Peduncle:

*Length.*—Long (approx. 63 cm).

*Cross section.*—Round.

*Tendency to fasciation.*—Absent.

*Thickness.*—Medium.

*Strength.*—Medium.

*Pubescence.*—Medium.

*Color.*—Medium green (R.H.S. 144A).

*Anthocyanin coloration.*—At base: medium (R.H.S. 184A). At top: absent.

*Involucral bracts.*—Absent.

PLANT

A. General appearance:

*Height.*—40 cm (exluding any flowers).

B. Foliage:

*Leaf blade.*—Length: medium-long (approx. 32±1 cm). Width: narrow (approx. 12.5±1 cm). Thickness: medium. Blistering: weak. Pubescence: On upper side (midrib excluded): dense. Depth of cuts or incisions in leaf: Basal part: deep. Central part: medium. Distal part: shallow. Color: Upper side of the leaf blade: medium green (R.H.S. 137B). Bottom side of the leaf blade: R.H.S. 138B. Glossiness on upper side: strong. Angle of apex: acute. Shape of apex: pointed. Margin of lobes: dentate. Number of lobes: approx. 11. Extensions of margin: small.

*Petiole.*—Petiole length: medium (approx. 16 cm). Color of petiole: R.H.S. 144A. Petiole anthocyanin coloration: medium, at bottom 20% R.H.S. 60A stripewise.

C. Disease resistance: No special disease resistance.

OTHER CHARACTERISTICS

An important characteristic for the variety 'Terwish' is the velvety, shiny color of the flower.

I claim:

1. A new and distinct cultivar of Gerbera plant named 'Terwish', substantially as herein shown and described, characterized particularly as to novelty by its characteristics enumerated above.

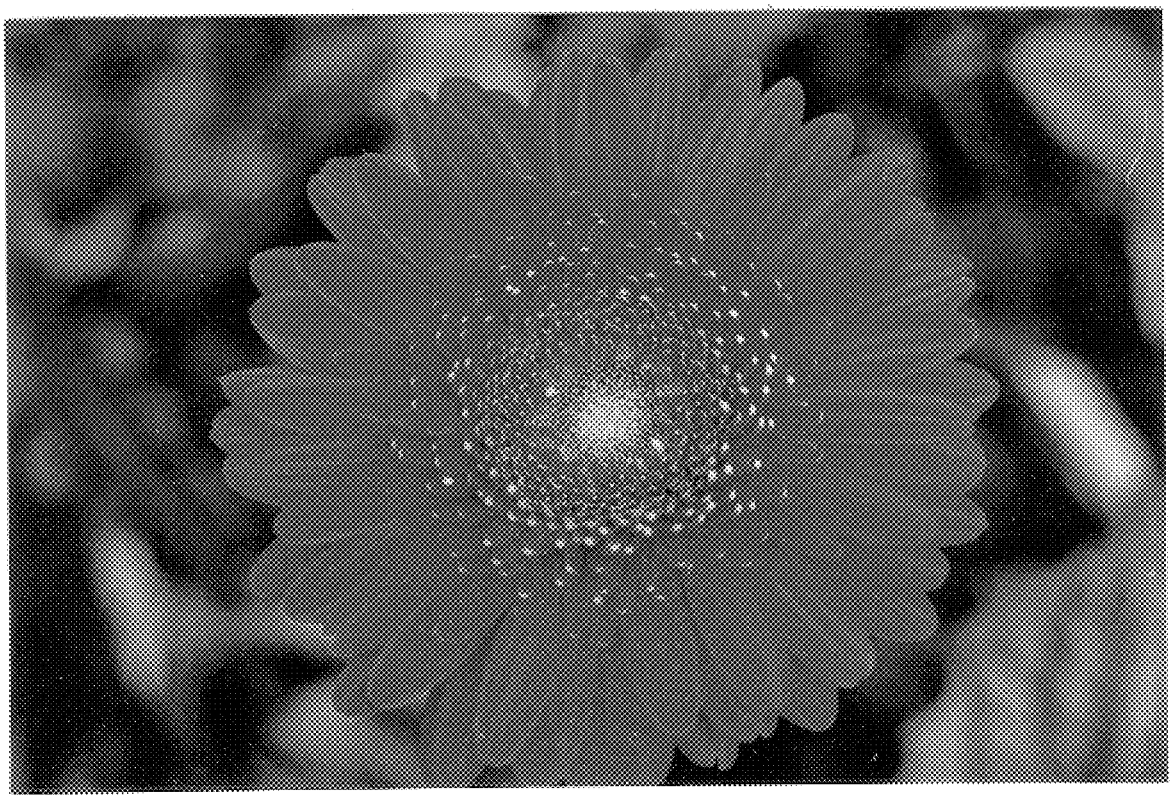
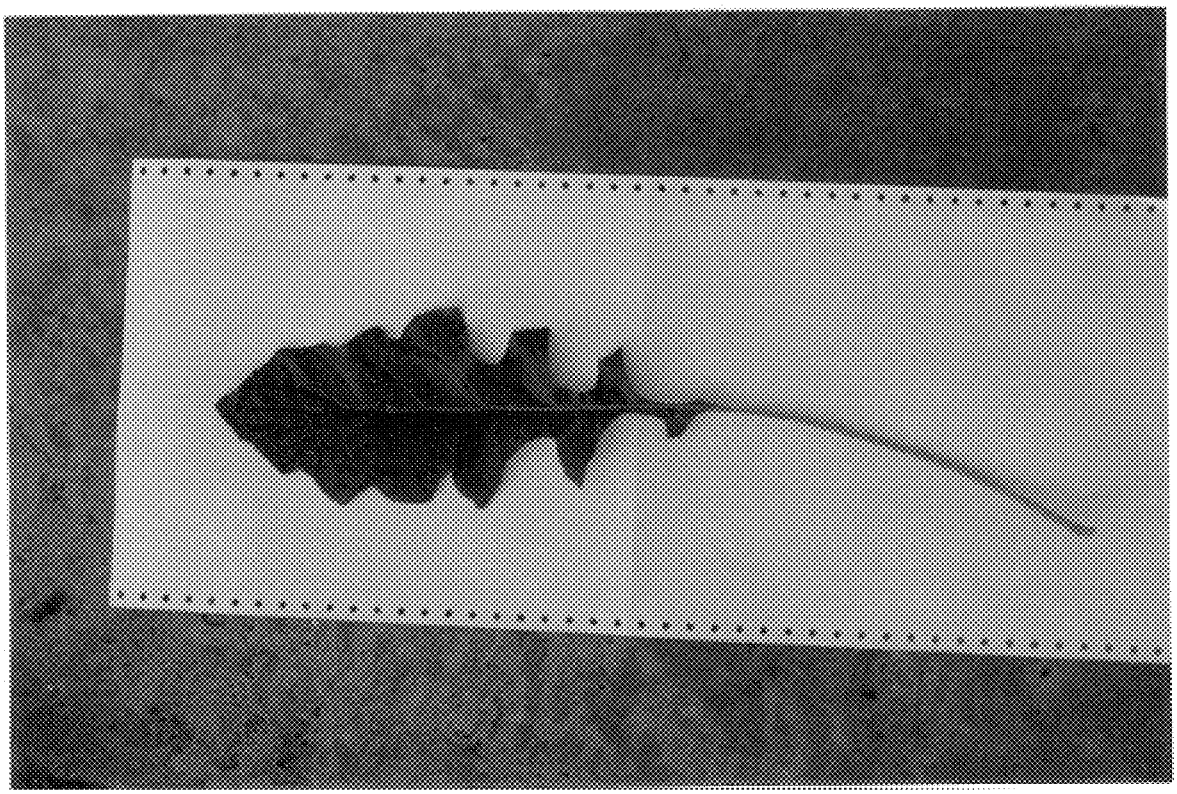

* * * * *